US00PP36256P2

(12) United States Plant Patent
Li

(10) Patent No.: US PP36,256 P2
(45) Date of Patent: Nov. 19, 2024

(54) ***VERBENA* PLANT NAMED 'KLEVP23124'**

(50) Latin Name: ***Verbena* x *hybrida***
Varietal Denomination: KLEVP23124

(71) Applicant: KLEMM + SOHN GMBH & CO. KG, Stuttgart (DE)

(72) Inventor: Ruijun Li, North Parramatta (AU)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/598,844

(22) Filed: Mar. 7, 2024

(51) Int. Cl.
*A01H 5/02* (2018.01)
*A01H 6/86* (2018.01)

(52) U.S. Cl.
USPC ..... Plt./308

(58) Field of Classification Search
USPC ..... Plt./308
See application file for complete search history.

*Primary Examiner* — Susan McCormick Ewoldt
*Assistant Examiner* — Zachariah Allan Kay
(74) *Attorney, Agent, or Firm* — Weatherly IP Solutions, LLC; James M. Weatherly

(57) ABSTRACT

A new Verbena plant particularly distinguished by round growth habit; good branching; and bicolour flower color with the upper two petals are purple, while the lower three petals are purple-violet, is disclosed.

1 Drawing Sheet

Genus and species: *Verbena* x *hybrida*.
Variety denomination: 'KLEVP23124'.

BACKGROUND OF THE NEW PLANT

The present invention comprises a new and distinct variety of Verbena, botanically known as *Verbena* x *hybrida*, and hereinafter referred to by the variety name 'KLEVP23124'. 'KLEVP23124' originated from a cross-pollination conducted in October 2019 in Cobbitty, New South Wales, Australia between the proprietary female Verbena variety '17.7144' (unpatented), and the commercial male 'KLEVP20052' (U.S. Plant Pat. No. 33,856).

The seeds from the cross were sown and plants were grown for evaluation, where an individual plant designated 'KLEVP23124' was selected from the group of plants in Cobbitty, New South Wales, Australia in October 2019.

In October 2019, 'KLEVP23124' was first vegetatively propagated by vegetative cuttings in Cobbitty, New South Wales, Australia. 'KLEVP23124' was found to reproduce true to type in successive generations of asexual propagation via vegetative cuttings.

SUMMARY

The following are the most outstanding and distinguishing characteristics of this new variety when grown under normal horticultural practices in Cobbitty, New South Wales, Australia.

1. Round growth habit;
2. Good branching; and
3. Bicolour flower color with the upper two petals that are purple, while the lower three petals are purple-violet.

DESCRIPTION OF THE PHOTOGRAPH

This new Verbena plant is illustrated by the accompanying photograph which shows the plant's overall plant habit including form, buds, foliage, and flowers. The photograph is of a plant approximately 12-weeks-old grown indoors in Stuttgart, Germany in May 2022. The colors shown are as true as can be reasonably obtained by conventional photographic procedures.

DESCRIPTION OF THE NEW VARIETY

The following detailed descriptions set forth the distinctive characteristics of 'KLEVP23124'. The data which define these characteristics were collected from asexual reproductions carried out in Cobbitty, New South Wales, Australia. Data was collected on three-month-old plants grown in 2020. Color references are to The R.H.S. Colour Chart of The Royal Horticultural Society of London (R.H.S.), 5$^{th}$ edition (2007).

Classification:
- *Family*.—Verbenaceae.
- *Botanical*.—*Verbena* x *hybrida*.
- *Common*.—Verbena.
- *Designation*.—'KLEVP23124'.

Parentage:
- *Female parent*.—'17.7144' (unpatented).
- *Male parent*.—'KLEVP20052' (U.S. Plant Pat. No. 33,856).

Plant:
- *Growth and branching habit*.—Upright with a compact and round shape.
- *Height* (*from top of soil*).—22.6 cm.
- *Width* (*horizontal plant diameter*).—33.0 cm.
- *Time to produce a finished flowering plant*.—Approximately 8 weeks.
- *Time to initiate and develop roots*.—2 weeks.
- *Root description*.—RHS 155B (White), fine fibrous roots.

Stems:
- *Number of branches per plant*.—More than 25.
- *Growth habit*.—Upright.
- *Length*.—20.0 cm.

*Diameter.*—0.26 cm.
*Internode length.*—2.1 cm.
*Color.*—RHS 139D (Green).
*Anthocyanin.*—Absent.
*Texture and appearance.*—Pubescent.

Leaves:
*Arrangement.*—Opposite.
*Immature and mature leaf.*—Color: Upper surface: RHS 141A (Green). Lower surface: RHS 141C (Green).
*Length.*—4.1 cm.
*Width.*—2.0 cm.
*Shape.*—Lanceolate.
*Apex.*—Acute.
*Base.*—Obtuse.
*Margin.*—Crenate.
*Texture.*—Upper surface: Leathery. Lower surface: Rugose.
*Venation type.*—Pinnate.
*Venation color.*—Upper surface: RHS 141D (Green). Lower surface: RHS 141D (Green).
*Petioles.*—Length: 0.3 cm. Diameter: 0.1 cm. Color: RHS 141D (Green). Texture: Leathery.

Flower buds:
*Shape.*—Tall, cylindrical.
*Length.*—1.5 cm.
*Diameter.*—0.3 cm.
*Color (at tight bud).*—RHS 68A.

Inflorescence:
*Blooming habit (flowering season).*—Continuously.
*Lastingness of individual blooms on the plant.*—About a week.
*Fragrance.*—Absent.
*Inflorescence type.*—Umbel.
*Length of inflorescence.*—4.6 cm.
*Diameter of inflorescence.*—4.9 cm.
*Number of florets per inflorescence.*—17.
*Peduncle.*—Color: RHS 141A (Green). Length: 2.5 cm. Diameter: 0.2 cm.

Florets:
*Length.*—1.8 cm.
*Diameter.*—1.7 cm.
*Texture.*—Smooth.
*Form.*—Single.
*Color.*—Immature: Upper surface: Upper two petals are RHS 78A (Purple) and the lower three petals distally, close to RHS N81A (Purple-violet) and proximally, close to 155D (white). Lower surface: Upper two petals are RHS 75B (Purple) and the lower three petals, distally, close to RHS 76C (Purple) and proximally, close to 155B (white). Mature: Upper surface: Upper two petals are RHS 77A (Purple) and the lower three petals distally, close to RHS N81B (Purple-violet) and proximally, close to 155D (white). Lower surface: Upper two petals are RHS 75A (Purple) and the lower three petals, distally, close to RHS 76C (Purple) and proximally, close to 155B (white).
*Corolla tube length.*—1.7 cm.
*Corolla tube color.*—RHS 157B.
*Petals.*—Length of lobe: 1.8 cm. Diameter of lobe: 0.8 cm. Lobe shape: Obtuse. Apex: Emarginate. Base: Fused. Margin: Entire. Texture: Upper surface: Glossy, satiny. Lower surface: Glossy, satiny.
*Pedicels.*—Not visible.

Sepals:
*Shape.*—Lanceolate.
*Apex.*—Acute.
*Base.*—Fused.
*Margin.*—Entire.
*Length.*—1.3 cm.
*Diameter.*—0.2 cm.
*Color.*—RHS 141C.
*Texture.*—Upper surface: Hairy, dull. Lower surface: Hairy, dull.

Reproductive organs:
*Stamens.*—Present.
*Quantity.*—4.
*Color.*—RHS 139D.
*Filament length.*—0.3 cm.
*Filament diameter.*—0.1 cm.
*Anther.*—Shape: Elliptic. Color: RHS 141D. Length: 0.15 cm. Diameter: 0.1 cm.
*Pollen amount.*—Sparse.
*Pistils.*—Number: 1. Length: 1.6 cm. Diameter: 0.1 cm. Stigma: Color: RHS 141D. Appearance: Ovate. Length: 0.1 cm. Diameter: 0.1 cm. Style: Color: RHS 141D. Length: 1.4 cm. Diameter: 0.1 cm. Appearance: Long.

Fruit and seed set: To date, fruit and seed development have not been observed on plants Disease and pest/insect resistance: Plants of 'KLEVP23124' have been observed to tolerate powdery mildew (*Podosphaera xanthii*).

COMPARISON WITH PARENTAL LINES AND KNOWN VARIETY

'KLEVP23124' is distinguished from its parents as described in Table 1.

TABLE 1

Comparison with Parental Lines

| Characteristic | 'KLEVP23124' | Female parent '1707144' | Male parent 'KLEVP20052' |
|---|---|---|---|
| Flower colour | Upper two petals are purple, while the lower three petals are purple-violet | Upper two petals are magenta, while the lower three petals are lavender | Upper two petals are red, while lower three petals are light violet |

'KLEVP23124' is most similar to the commercial Verbena variety 'KLEVP15616' (U.S. Plant Pat. No. 28,320). Differences between the varieties are described in Table 2.

TABLE 2

Comparison with Similar Variety

| Characteristic | 'KLEVP23124' | 'KLEVP15616' |
|---|---|---|
| Growth habit | Round | Upright |
| Branching ability | Better branching than 'KLEVP15616' | Less branching than KLEVP23124 |
| Flower colour | Bicolour | Solid color with eyes |

I claim:

1. A new and distinct variety of Verbena plant designated 'KLEVP23124' as illustrated and described herein.

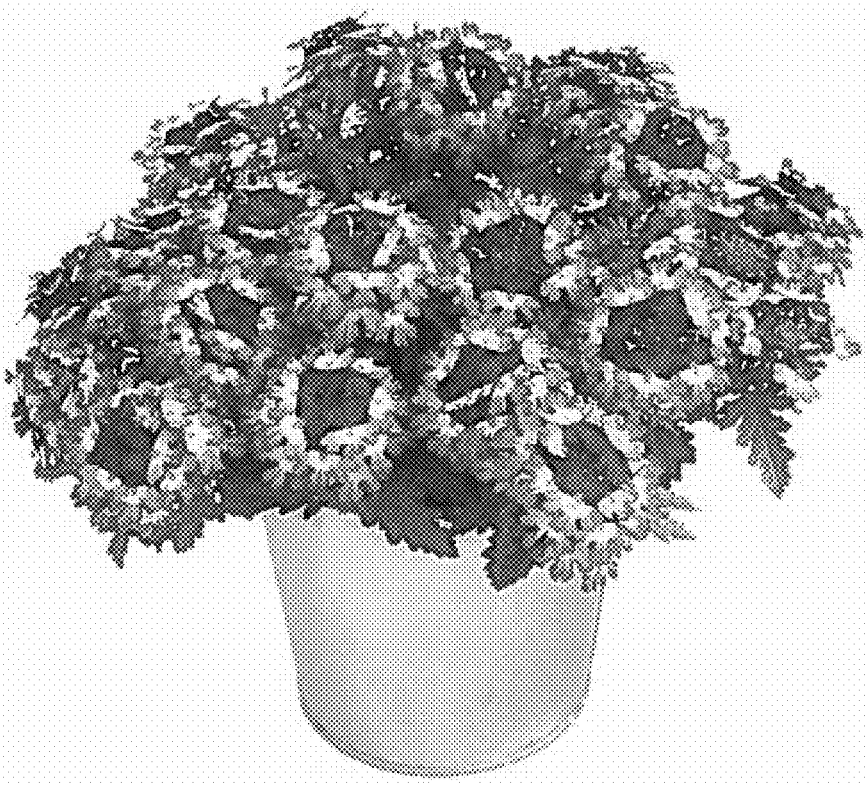

* * * * *